United States Patent [19]

Falbe et al.

[11] 4,039,584

[45] Aug. 2, 1977

[54] CATALYTIC CLEAVAGE OF ISOBUTYRALDEHYDE

[75] Inventors: Jurgen Falbe, Dinslaken; Hans Tummes; Heinz-Dieter Hahn, both of Oberhausen-Sterkrade-Nord, all of Germany

[73] Assignee: Ruhrchemie Aktiengesellschaft, Oberhausen-Holten, Germany

[21] Appl. No.: 633,334

[22] Filed: Nov. 19, 1975

Related U.S. Application Data

[63] Continuation of Ser. No. 864,153, Oct. 6, 1969, abandoned.

[30] Foreign Application Priority Data

Apr. 3, 1969 Germany .............................. 1917244

[51] Int. Cl.² ............................................. C07C 45/08
[52] U.S. Cl. .............................. 260/604 HF; 252/373; 260/682
[58] Field of Search ..................... 260/604 HF, 682; 252/373

[56] References Cited

U.S. PATENT DOCUMENTS

| 2,694,735 | 11/1954 | Hull et al. ................... 260/604 HF |
|---|---|---|
| 2,930,765 | 3/1960 | Cooper et al. ............... 260/604 HF |
| 3,222,132 | 12/1965 | Dowden ....................... 252/373 |
| 3,535,400 | 10/1970 | Falbe et al. .................. 260/682 |
| 3,541,729 | 11/1970 | Dantowitz .................... 252/373 |
| 3,578,423 | 5/1971 | Falbe et al. .................. 252/373 |

FOREIGN PATENT DOCUMENTS 1,099,914 1/1968 United Kingdom ................. 252/373

OTHER PUBLICATIONS

Hemidy et al, Bull. Soc. Chim., France, (1965), pp. 1710–1714.
Tsuji et al, JACS, 90 (1968), pp. 94–98.
Shubert et al, Chemistry of the Carbonyl Group, 1966, pp. 747–749.

*Primary Examiner* — Howard T. Mars
*Attorney, Agent, or Firm* — Burgess, Dinklage & Sprung

[57] ABSTRACT

Isobutyraldehyde is cleaved to form propylene, carbon monoxide and hydrogen over a supported rhodium and/or platinum catalyst at a temperature of 200° to 400° C and a pressure of 0.1 to 20 atmospheres. Preferably the isobutyraldehyde is obtained from the oxo synthesis of n-butyraldehyde from propylene and the gases resulting from the cleavage are returned to the oxo synthesis step.

12 Claims, No Drawings

CATALYTIC CLEAVAGE OF ISOBUTYRALDEHYDE

This is a continuation of application Ser. No. 864,153, filed Dec. 6, 1969, and now abandoned.

PRIOR ART

The oxo synthesis of hydroformylation of olefins, i.e., the catalytic reaction of compounds having olefinic double bonds with carbon monoxide and hydrogen, always results in the formation of isomeric aldehyde mixtures, except when symmetrical compounds are used which are not isomerizable by double-bond migration (cf. J. Falbe, "Synthesen mit Kohlenmonoxyd," Springer-Verlag, Berlin-Heidelberg-New York, 1967, pp. 7 et seq.). For example, n-butyraldehyde and isobutyraldehyde are formed together from propylene in an approximate ratio of 4:1. This ratio cannot be substantially increased by changing the conditions of the reaction. Whereas, n-butyraldehyde represents a valuable starting material for many reactions, it has not been possible hitherto to find a corresponding economical use for the iso compound.

The problem therefore exists of converting isobutyraldehyde into compounds which are commercially exploitable, without losing sight of the economic factors involved. Particularly good prospects seem to be offered by the cleavage of isobutyraldehyde in reversal of the equation of its formation by the oxo synthesis to produce propylene, carbon monoxide and hydrogen, as follows:

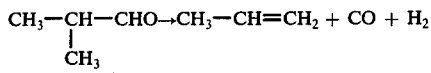

By putting the gas mixture that thus results back into the oxo synthesis, it is possible to increase considerably the yield of n-butyraldehyde from a given quantity of propylene, while reducing the amount of isobutyraldehyde that is inevitably produced.

The catalytic cleavage of isobutyraldehyde with the formation of propylene is known (H. J. Hagemeyer and G. C. De Croes, "The Chemistry of Isobutyraldehyde," Tennessee Eastman Co., 1954, p. 55). Palladium and copper were used as the catalysts according to this reference. Copper however has only a very slight activity, and with palladium the propylene that initially forms is to a great extent hydrogenated to yield propane. Consequently when the more active palladium is used both propylene and hydrogen are consumed and are no longer available for reuse in the oxo synthesis.

The decarbonylation of aldehydes will take place in the presence of a palladium catalyst (J. Tsuji and K. Ohmo, J. Amer. Chem. Soc. 90, 94 (1968). Aldehydes of higher molecular weight having boiling points above 200° C were according to this reference reacted in the liquid phase, and lower boiling aldehydes were reacted in the gaseous phase. The cleavage products were mostly saturated compounds and carbon monoxide; the olefinic compounds being formed to a much lesser extent.

According to the research of J. F. Hemidy and F. G. Gault (Bull. Soc. Chem. France 1965, pp. 1710–14), butyraldehyde is cleaved on a palladium film to a mixture of propylene, propane, carbon monoxide and hydrogen. As the reaction continues, however, the propylene and hydrogen react, with the formation of propane.

The reaction of isobutyraldehyde with complex ruthenium compounds also results in propylene as a reaction product, (R. H. Prince and K. A. Raspin, Chem. Comm. 1966, p. 156). This reaction requires a stoichiometric use of aldehyde and ruthenium compounds, and for this reason alone it is not suitable for commercial application.

It is also possible to cleave aldehydes on catalytic quantities of chlorotri-(triphenylphosphine)-rhodium (K. Ohno and J. Tsuji, J. Amer. Chem. Soc. 90, 99–107 [1968]). In this procedure, too, mostly saturated hydrocarbons are formed, while olefinically unsaturated compounds are produced only in low yields.

THIS INVENTION

It has now been found that good results can be achieved in the catalytic cleavage of isobutyraldehyde with the formation of gas mixtures consisting mainly of propylene, carbon monoxide and hydrogen by reacting isobutyraldehyde in the gaseous phase, at temperatures from 200° to 400° C and at pressures of 0.1 to 20 atm, over catalysts comprising rhodium and/or platinum with the catalyst preferably being suitably supported.

Although at a temperature of 200° to 400° C, the propane-propylene equilibrium is entirely on the side of the saturated hydrocarbon, and both rhodium and platinum are hydrogenation catalysts, the formation of propane is surprisingly suppressed to a large extend and propylene is suprisingly obtained in excellent yields.

The rhodium and/or platinum catalysts are used in the form of supported catalysts, using such customary support materials as aluminum oxide and silica, or mixtures thereof. Impregnated catalysts in which the catalytically active noble metals are concentrated on the surface of the support have proved particularly effective. Such catalysts are prepared in a known manner by treating preformed supports, such as pellets, balls or strings with an aqueous solution of the metal salt, e.g., the nitrate, drying calcining, and reducing with hydrogen or other reducing agents. The catalysts preferably contain 0.01 to 2, especially 0.2 to 0.5 weight percent of active metal, based on the total weight of the catalyst.

According to a preferred embodiment of this invention, a temperature in the range of 280° to 330° C is used. Below 250° C the reaction is incomplete so that part of the isobutyraldehyde remains unaltered and above 400° C, carbon deposition occurs as a result of secondary reactions, resulting in a diminution of the activity of the catalyst.

The selectivity of the cleavage in the range from 200° to 400° C is largely independent of the reaction temperature. An increase in the selectivity and an improvement in the yield of the desired products can be achieved by performing the reaction in the presence of water vapor. The amount of water vapor added depends on the pressure. The amount of water vapor can be 0.3 to 20 moles of water vapor per mole of isobutyraldehyde. The partial pressure of the dry gases to be cleaved should not exceed about 3.0 atm, if optimum selectivity is to be achieved. Good results are obtained if an amount of water ranging between 0.3 and 1.0 mole is used for each mole of isobutyraldehyde and for each 0.3 to 1 atmosphere of the pressure that is applied if the reaction is carried out at a pressure greater than atmospheric.

For example, if the total pressure is 10 atm, 5 to 25 moles of water vapor are added per mole of isobutyraldehyde.

The high activity of the catalyst used according to the invention assures that the isobutyraldehyde will be substantially reacted even with a high feed rate. For example, at a rate of 2 volumes of liquid isobutyraldehyde per volume of catalyst (corresponding to about 500 volumes of vaporous aldehyde per volume of catalyst), at a temperature in the preferred temperature range of 280° to 300° C, and at reaction pressures of 0.1 to 3.0 atm, the cleavage is still greater than 90 percent. When reaction pressures of 10 to 20 atm are used, and a water vapor excess of 20 moles of steam per mole of isobutyraldehyde is added, the feed rate can even be as high as 3 to 4 volumes of liquid isobutyraldehyde per volume of catalyst at a 90 percent or greater cleavage level. It is desirable not to use an excessively low feed rate, because the hydrogenating action of the catalyst tends to convert the propylene to propane.

The noble metal catalysts used for the cleavage of isobutyraldehyde have been found to have adequate long-term activity. Any loss of activity that may occur can be compensated by slight elevation of the reaction temperature. Spent catalysts can be regenerated by treatment with oxygen-containing gases, such as air, at temperatures of 350° to 500° C, followed by reduction, in a known manner.

The cleavage of isobutyraldehyde to propylene, carbon monooxide and hydrogen can be performed at atmospheric pressure, or at elevated or reduced pressures. It has proved particularly desirable to use pressures of 0.1 to 20 atm.

The starting product is particularly the isobutyraldehyde that results from the hydroformylation of propylene, which contains no impurities harmful to the catalysts, and which can be cleaved without preliminary treatment. Isobutyraldehyde of different origin can, of course, be used but care must be taken to see that the material entering the reactor contains as little sulfur as possible. If necessary, the aldehyde can be desulfurized first, by known methods.

Tubular reactors of conventional construction can be used for the performance of the process of the invention. The isobutyraldehyde is first vaporized in a preheater and superheated, and then passed over the catalyst, together with steam. The separation of the gas mixture produced by the cleavage into a propylene-propane fraction and a $CO + H_2$ fraction can be performed by known methods, e.g., by pressure separation or by washing.

Preferably, the cleavage products are used again in the oxo synthesis from which the isobutyraldehyde starting product originated. By the return of the propylene-propane fraction to the olefin input and the return of the $CO + H_2$ fraction to the synthesis gas of the propylene hydroformylation, a considerable saving of propylene and synthesis gas is achieved as regards the production of n-butyraldehyde. Since the entire isobutyraldehyde yield from the oxo-step can be reused in the hydroformylation after cleavage according to the procedure of the invention, the present invention provides a way of transforming propylene almost totally by oxo synthesis into n-butyraldehyde or n-butanol, as the case may be.

EXAMPLES

EXAMPLE 1

A rhodium-containing catalyst having a rhodium content of 0.5 percent of the weight of the formed catalyst was prepared as follows:

99.5 g. of a pre-shaped γ-aluminum oxide was suspended in a solution of 1.32 g $RhCl_3 . 3 H_2O$ in 100 ml of water and left to stand at 80° C until the solution lost its color entirely. After decantation and washing with water, the catalyst was first air dried for 10 hours at 130° to 140° C, then calcined for 15 hours at 500° C, and then then was reduced with hydrogen at 300° C.

Platinum and platinum/rhodium catalysts can be similarly prepared.

The cleavage of the isobutyraldehyde was performed in an externally heated quartz tube (inside diameter 23 mm) at 330° C and at a pressure of 1 atm. 225 ml of isobutyraldehyde per hour was vaporized in a preheater, superheated to 350° C, and fed downward through 100 ml of catalyst. The cleavage gas, consisting of propene, CO and hydrogen, was chilled by means of a cooler to 0° C, whereupon the unreacted isobutyraldehyde and the water dissolved in the starting aldehyde condensate. Any remaining isobutyraldehyde was separated in a condensing trap which was refrigerated to −20° C and filled with glass wool. The quantity of the cleavage gas was measured with a gas meter and its composition was determined by gas chromatography. The conversion was 98 percent. Composition of cleavage gas was:

|  | Vol % | Moles per 100 moles of transformed isobutyraldehyde |
|---|---|---|
| Propene | 31.1 | 85.8 |
| Carbon monoxide | 35.8 | 98.8 |
| Hydrogen | 28.2 | 78.0 |
| Propane | 4.8 | 13.3 |
| Carbon dioxide | 0.1 | 0.3 |

In addition, 0.9 percent of the aldehyde input was hydrogenated to isobutanol.

EXAMPLE 2

As in Example 1, a rhodium catalyst on a γ-aluminum oxide support was prepared, having a content of 0.1 percent Rh by weight. Isobutyraldehyde was cleaved at 300° C at a feed rate of 0.9 volume per volume per hour (aldehyde as liquid) by the method described in Example 1. The conversion was 69 percent. The product gas had the following composition:

|  | Vol % | Moles per 100 moles of isobutyraldehyde transformed |
|---|---|---|
| Propene | 32.7 | 94.1 |
| Carbon monoxide | 34.8 | 100.0 |
| Hydrogen | 30.7 | 88.3 |
| Propane | 0.8 | 2.4 |
| Carbon dioxide | 1.0 | 3.0 |

1.5 percent of the input isobutyraldehyde was hydrogenated to isobutanol.

EXAMPLE 3

A mixture of isobytyraldehyde and water vapor was passed over a rhodium catalyst as described in Example 1 having a metal content of 0.5 percent Rh by weight.

Ninety (90) ml (82 g) of isobutyraldehyde and 12 g of water were vaporized together and superheated to 300° C. The cleavage was performed by the procedure described in Example 1, at a temperature of 300° C and a feed rate of 0.9 V/V/h, (the isobutyraldehyde being calculated as liquid). At a conversion of 92 percent, the product composition was:

|  | Vol-% | Moles per 100 moles of isobutyraldehyde transformed |
|---|---|---|
| Propene | 32.5 | 91.8 |
| Carbon monoxide | 35.4 | 100.1 |
| Hydrogen | 29.3 | 82.8 |
| Propane | 1.8 | 5.1 |
| Carbon dioxide | 1.0 | 2.8 |

Also, 1.3 percent of the reacted isobutyraldehyde was transformed to isobutanol.

EXAMPLE 4

A platinum catalyst on a γ-aluminum support was prepared as described in Example 1, with a content of 0.1 percent Pt by weight. Isobutyraldehyde was cleaved at 300° C by the method described in Example 1, at a feed rate of 0.9 V/V/h (the aldehyde being calculated as liquid).

The conversion amounted to 53% and the product gas had the following composition:

|  | Vol-% | Moles per 100 moles of reacted isobutyraldehyde |
|---|---|---|
| Propene | 29.2 | 79.8 |
| Carbon monoxide | 37.0 | 101.2 |
| Hydrogen | 28.8 | 78.8 |
| Propane | 4.9 | 13.4 |
| Carbon dioxide | 0.1 | 0.3 |

4.6 percent of the reacted isobutyraldehyde was hydrogenated to isobutanol.

EXAMPLE 5

A rhodium catalyst on a γ-aluminum oxide support was prepared as in Example 1, with a metal content of 0.5 percent Rh by weight. 1680 ml of isobutyraldehyde was vaporized per hour in a preheater, superheated to 350° C, and passed through an externally heatable high-grade sreel tube filled with 700 ml of Rh-γ-Al₂O₃. With the aid of a pressure maintenance valve the cleavage reaction was performed at a pressure of 5 atmospheres gauge. The reaction temperature was 290° C. After the pressure was reduced to 1 atm, the cleavage products and the unreacted isobutyraldehyde were captured and analysed, as described in Example 1. At a conversion of 80 percent, the gas had the following composition:

|  | Vol-% | Moles per 100 moles of reacted isobutyraldehyde |
|---|---|---|
| Propene | 27.8 | 72.0 |
| Carbon monoxide | 37.6 | 97.0 |
| Hydrogen | 24.5 | 63.2 |
| Propane | 9.0 | 23.2 |
| Carbon dioxide | 1.1 | 2.8 |

3.9 percent of the reacted isobutyraldehyde was hydrogenated to isobutanol.

EXAMPLE 6

Isobutyraldehyde was cleaved as described in Example 5, but in the presence of 1 mole of water vapor per mole of isobutyraldehyde, over a rhodium catalyst having a metal content of 0.5 percent Rh by weight, at a pressure of 5 atm and a temperature of 300° C. The feed rate amounted to 2.4 V/V/h (the isobutyraldehyde being calculated as liquid). At a conversion of 51 percent, the gas had the following composition:

|  | Vol-% | Moles per 100 moles of reacted isobutyraldehyde |
|---|---|---|
| Propene | 29.5 | 8.14 |
| Carbon monoxide | 36.2 | 99.6 |
| Hydrogen | 28.4 | 78.0 |
| Propane | 5.6 | 15.4 |
| Carbon dioxide | 0.3 | 0.8 |

2.5 percent of the isobutyraldehyde was hydrogenated to isobutanol.

EXAMPLE 7

Isobutyraldehyde was cleaved over a rhodium catalyst on a γ-aluminum support prepared as in Example 1 with a metal content of 0.5 percent Rh by weight, the cleavage being performed in a partial vacuum. The absolute pressure was 200 Torr, the temperature 300° C and the catalyst loading 0.9 V/V/h (aldehyde being calculated as liquid).

At a conversion of 83 percent the gas had the following composition.

|  | Vol-% | Moles per 100 moles of reacted isobutyraldehyde |
|---|---|---|
| Propene | 31.0 | 89.0 |
| Carbon monoxide | 34.7 | 100.0 |
| Hydrogen | 31.0 | 89.0 |
| Propane | 3.3 | 9.6 |
| Carbon dioxide | 0.1 | 0.3 |

In addition, 1.0 percent of the isobutyraldehyde was hydrogenated to isobutanol.

EXAMPLE 8

In the manner described in Example 1, 400 ml of a rhodium catalyst on γ-aluminum oxide supports was prepared having a metal content of 0.24 percent rhodium by weight. 1200 ml of isobutyraldehyde and 4800 ml of water were vaporized per hour in a preheater, superheated to 350° C, and passed through an externally heated high-grade steel pipe filled with the catalyst. The reaction was performed at a pressure of 10 atmospheres gauge. The reaction temperature was 290° C. After the pressure was dropped to 1 atm, the cleavage products and the aqueous condensate solution containing isobutyraldehyde were captured and analyzed. At a conversion of 80 percent the product gas had the following composition:

|  | Vol-% | Moles per 100 moles of reacted isobutyraldehyde |
|---|---|---|
| Propylene | 29.5 | 87.4 |
| Carbon monoxide | 29.8 | 88.4 |
| Hydrogen | 32.8 | 97.2 |
| Propane | 2.8 | 8.3 |
| Carbon dioxide | 5.1 | 15.0 |

2.4 percent of the reacted isobutyraldehyde was hydrogenated to isobutanol.

We claim:
1. In a process of hydroformylating propylene with carbon monoxide and hydrogen to form a mixture of normal and isobutyraldehydes, the improvement comprising separating said isobutyraldehydes, converting the so separated isobutyraldehyde at a temperature in the range of 200° to 400° C and a pressure in the range of 0.1 to 20 atmospheres in the presence of rhodium as catalyst for the conversion to produce a gas mixture consisting predominately of propylene, carbon monoxide, and hydrogen, and returning propylene, carbon monoxide, and hydrogen of said gas mixture to the hydroformylating step.

2. The process of claim 1 wherein said rhodium is on a support and the amount of rhodium is in the range of 0.01 to 2 percent by weight with reference to the total weight of catalyst, and wherein water in an amount in the range of 0.3 to 20 moles per mole of isobutyraldehyde is added during said conversion.

3. Process, according to claim 2, the support being aluminum oxide, silica or a mixture thereof.

4. In a process for the catalytic cleavage of isobutyraldehyde to form a gas consisting predominately of propylene, carbon monoxide and hydrogen, the improvement comprising reacting the isobutyraldehyde in the gaseous phase at a temperature in the range of 200° to 400° C and a pressure in the range of 0.1 to 20 atm. in the presence of rhodium as catalyst for the reaction.

5. The process of claim 4, wherein said rhodium is on a support and the amount of rhodium is in the range of 0.01 to 2 percent by weight with reference to the total weight of the catalyst.

6. The process of claim 5, wherein the catalyst is impregnated on the support.

7. The process of claim 4, wherein said temperature is in the range from 280° to 330° C.

8. The process of claim 7, wherein for each mole of isobutyraldehyde and for every 0.3 to 1 atm. of pressure, there is used 0.3 to 1 mole of water.

9. The process of claim 4, wherein the cleavage is performed in the presence of in the range of 0.3 to 20 moles of water vapor per mole of isobutyraldehyde.

10. The process of claim 5, wherein for each mole of isobutyraldehyde and for every 0.3 to 1 atm. of pressure, there is used 0.3 to 1 mole of water.

11. Process, according to claim 6, the support being aluminum oxide, silica or a mixture thereof.

12. Process according to claim 5, wherein the temperature is above 250° C.

* * * * *

UNITED STATES PATENT AND TRADEMARK OFFICE
CERTIFICATE OF CORRECTION

PATENT NO. : 4,039,584
DATED : August 2, 1977
INVENTOR(S) : Jurgen Falbe, Hans Tummes and, Heinz-Dieter Hahn It is certified that error appears in the above-identified patent and that said Letters Patent are hereby corrected as shown below:

Column 1, line 8, change "of" (first occurrence) to --or--.

Column 5, line 47, change "sreel" to --steel--.

Column 6, line 27, change "83" to --82--.

Column 7, line 2, change "isobutyraldehydes" to --isobutyraldehyde--.

Signed and Sealed this

First Day of November 1977

[SEAL]

Attest:

RUTH C. MASON
Attesting Officer

LUTRELLE F. PARKER
Acting Commissioner of Patents and Trademarks